(12) United States Patent
Wang et al.

(10) Patent No.: US 7,458,551 B2
(45) Date of Patent: Dec. 2, 2008

(54) SAFETY RECEPTACLE FOR A NEEDLE OF AN INTRAVENOUS DRIP ASSEMBLY

(75) Inventors: Shih-Chun Wang, Chia-Yi (TW); Kiwi Yuan, Taipei (TW); Jia-Ming Chang, Taipei Hsien (TW)

(73) Assignee: Biotop Holding Co., Ltd., Grand Cayman (KY)

( * ) Notice: Subject to any disclaimer, the term of this patent is extended or adjusted under 35 U.S.C. 154(b) by 571 days.

(21) Appl. No.: 11/274,663

(22) Filed: Nov. 15, 2005

(65) Prior Publication Data

US 2007/0112315 A1    May 17, 2007

(51) Int. Cl.
    *A47F 5/00*    (2006.01)
(52) U.S. Cl. ...................... 248/313; 248/689
(58) Field of Classification Search .......... 604/110, 604/192, 263, 257; 248/309.1, 313, 314, 248/74.1, 74.2, 539, 682, 689, 540, 541, 248/75, 78, 79, 154, 311.3
    See application file for complete search history.

(56) References Cited

U.S. PATENT DOCUMENTS

| | | | | |
|---|---|---|---|---|
| 1,647,039 A | * | 10/1927 | Fischer | 248/309.1 |
| 4,486,044 A | * | 12/1984 | Gordon et al. | 294/31.2 |
| 5,356,395 A | * | 10/1994 | Chen | 604/263 |
| 6,189,488 B1 | * | 2/2001 | Goldsher et al. | 119/72 |
| 6,893,067 B1 | * | 5/2005 | Ayala | 294/15 |
| 7,108,678 B2 | * | 9/2006 | Hsieh et al. | 604/110 |
| 2005/0148930 A1 | | 7/2005 | Hsieh et al. | |

FOREIGN PATENT DOCUMENTS

TW    516439    1/2003

\* cited by examiner

*Primary Examiner*—Ramon O Ramirez
(74) *Attorney, Agent, or Firm*—William E. Pelton, Esq.; Cooper & Dunham LLP

(57) ABSTRACT

The safety receptacle is used with an intravenous drip assembly having an intravenous drip, a needle and a tip protector and has a front bracket, a connecting bracket, a rear bracket, at least one C-clip and two clipping sheets. The C-clip is formed on the front bracket to hold the intravenous drip. The clipping sheets are mounted pivotally between the front and rear brackets. The needle can be held in and removed out from the tip protector. The tip protector can be held in the safety receptacle by the clipping sheets. When the clipping sheets are pivoted, the tip protector is released and can be removed from the safety receptacle.

4 Claims, 5 Drawing Sheets

SAFETY RECEPTACLE FOR A NEEDLE OF AN INTRAVENOUS DRIP ASSEMBLY

BACKGROUND OF THE INVENTION

1. Field of the Invention

The present invention relates to a safety receptacle, especially to a safety receptacle for a needle of an intravenous drip assembly.

2. Description of the Prior Art

Intravenous drip assemblies are used to infuse medicinal liquid such as nutriments, blood and medicine into patients. The intravenous drip assembly comprises an intravenous drip, an infusion tube and a needle. The infusion tube has two ends. The two ends of the infusion tube connect respectively to the intravenous drip and the needle so the infusion tube carries medicinal liquid from the intravenous drip to the needle. The intravenous drip is held on a support. The needle is inserted into a vein to inject the medicinal liquid. When the needle is removed from the vein, a tip protector is mounted on and covers the needle to keep a contaminated needle from accidentally stabbing people. However, the user who removes the needle from the vein needs to remove the needle with one hand and hold the tip protector with the other hand. When the needle is inserted into the tip protector, the needle easily stabs the user.

Therefore, a safety receptacle is attached to the support to hold the needle. Because the safety receptacle is attached to the support and is not handled by a user, the needle will not stab the user when the needle is inserted into the safety receptacle. The conventional safety receptacle has a fastening device to fasten the needle and to keep the needle from being removed from the conventional safety receptacle. However, the needle may be removed from the vein momentarily and need to be inserted into the vein again. A needle retracted into the conventional safety receptacle cannot be removed from the conventional safety receptacle so the needle cannot be used.

To overcome the shortcomings, the present invention provides an improved safety receptacle for a needle of an intravenous drip to mitigate or obviate the aforementioned problems.

SUMMARY OF THE INVENTION

The main objective of the present invention to provide a safety receptacle for a needle of an intravenous drip assembly having an intravenous drip, a needle and a tip protector, which is safer than a conventional safety receptacle and from which the needle can be removed and used again. The safety receptacle has a front bracket, a connecting bracket, a rear bracket, at least one C-clip and two clipping sheets. The C-clip is formed on the front bracket to hold the intravenous drip. The clipping sheets are mounted pivotally between the front and rear brackets. The needle can be received in and removed from the tip protector. The tip protector can be held in the safety receptacle by the clipping sheets. When the clipping sheets are pivoted, the tip protector is released and can be removed from the safety receptacle.

Other objectives, advantages and novel features of the invention will become more apparent from the following detailed description when taken in conjunction with the accompanying drawings.

DETAILED DESCRIPTION OF THE PREFERRED EMBODIMENTS

Figure 3:
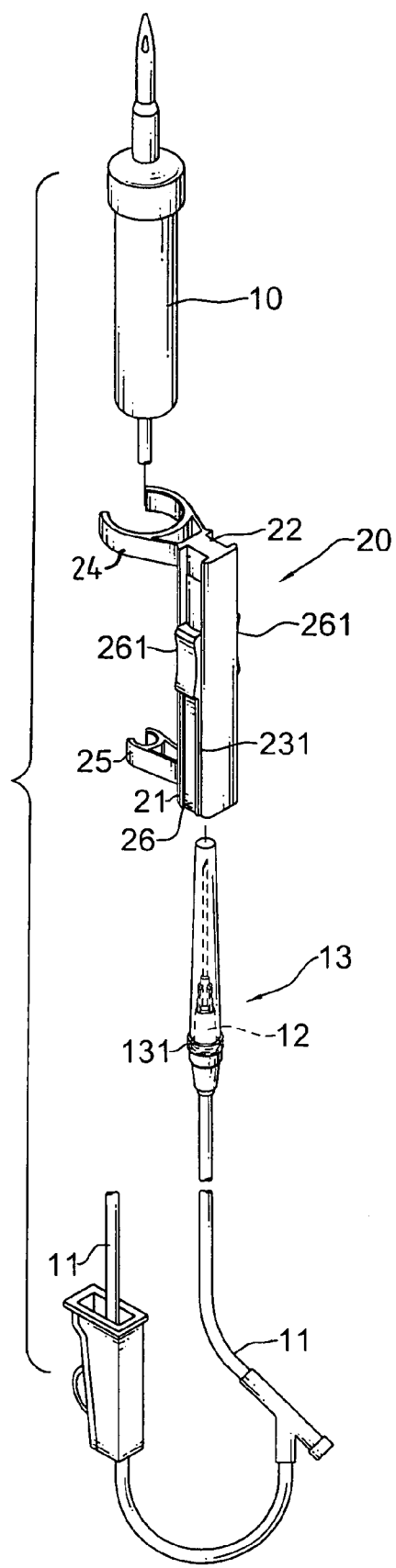
FIG. 3 is an exploded perspective view of the intravenous drip assembly with the safety receptacle in FIG. 1.

With reference to FIG. 3, a safety receptacle (20) in accordance with the present invention is used with an intravenous drip assembly having an intravenous drip (10), an infusion tube (11), a needle (12) and a tip protector (13). The infusion tube (11) has two ends. The two ends of the infusion tube (11) connect respectively to the intravenous drip (10) and the needle (12). The tip protector (13) is mounted on and covers the needle (12) and has an opening and an annular flange (131). The annular flange (131) is formed around the tip protector (13) adjacent to the opening.

Figure 1:
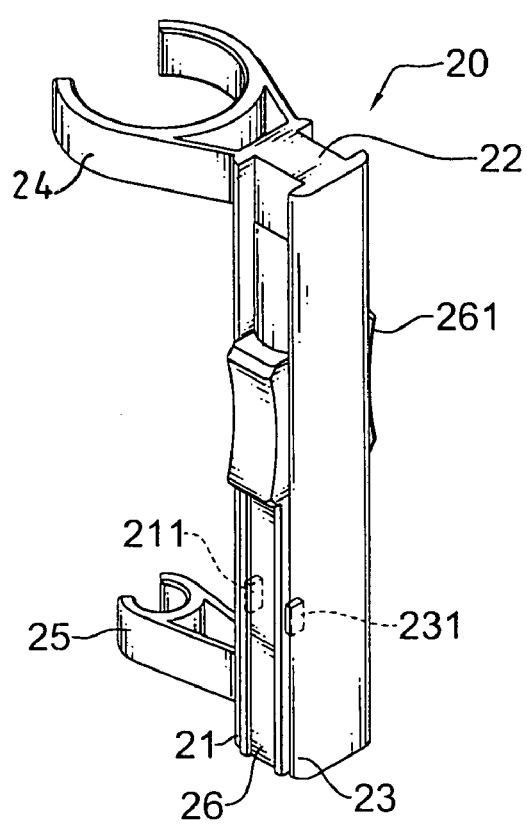
FIG. 1 is a perspective view of a safety receptacle for a needle of an intravenous drip assembly in accordance with the present invention.
Figure 2:
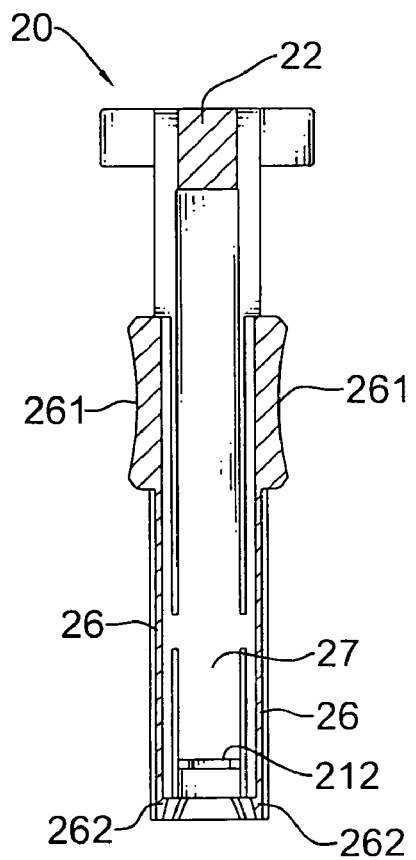
FIG. 2 is a rear view in partial section of the safety receptacle in FIG. 1.

With further reference to FIGS. 1 and 2, the safety receptacle (20) comprises a front bracket (21), a connecting bracket (22), a rear bracket (23), at least one C-clip (24, 25), two clipping sheets (26) and an inner cavity (27).

The front bracket (21) has an upper end, a lower end, an outside surface, an inside surface, two sides, two protrusions (211) and a limit (212). The protrusions (211) are formed on the inside surface near the lower end adjacent respectively to the two sides. The limit (212) is formed on and extends out from S the inside surface near the lower end.

Figure 7:
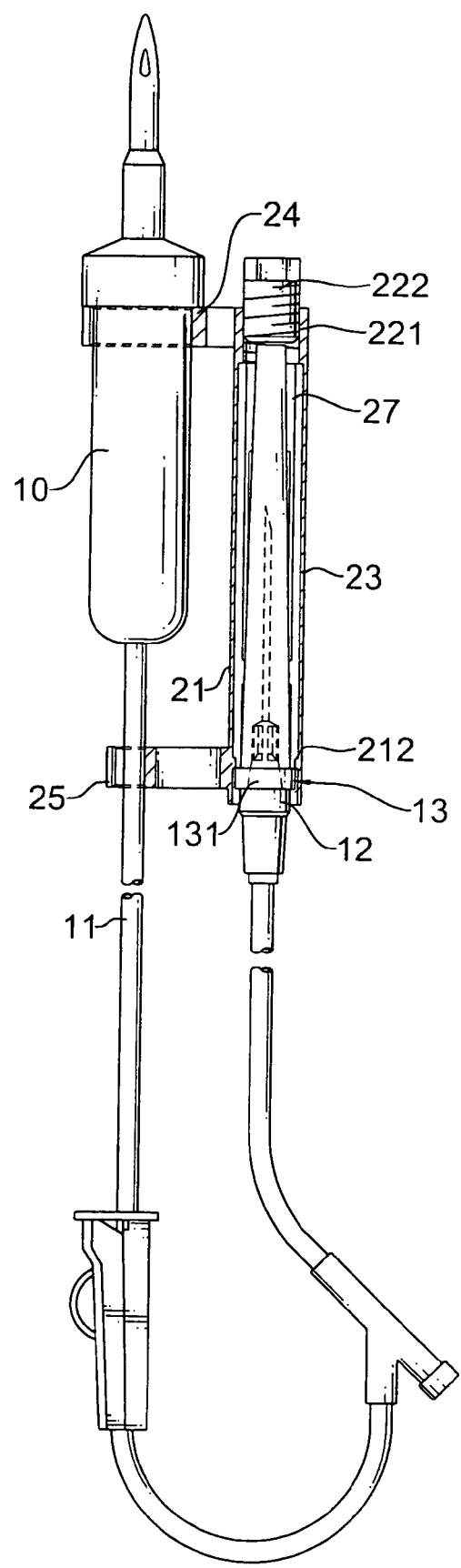
FIG. 7 is a side view in partial section of the intravenous drip assembly with another safety receptacle in accordance with the present invention.

With further reference to FIG. 7, the connecting bracket (22) is formed on and extends transversely out from the inside surface of the front bracket (21) adjacent to the upper end and has a front end, a rear end, an optional threaded hole (221) and an optional threaded adjustment plug (222). The front end of the connecting bracket (22) is formed on the inside surface of the front bracket (21). The threaded hole (221) is formed longitudinally through the connecting bracket (22). The threaded adjustment plug (222) screws into the threaded hole (221).

The rear bracket (23) is formed on and extends longitudinally out from the rear end of the connecting bracket (22) and has an upper end, a lower end, an inside surface, two sides and two protrusions (231). The inside surface is adjacent to the upper end of the rear bracket (23) and is formed on the rear end of the connecting bracket (22). The protrusions (231) are formed on the inside surface of the rear bracket (23), are adjacent respectively to the two sides of the rear bracket (23) and correspond to the protrusions (211) on the front bracket (21).

The at least one C-clip (24, 25) is formed on and extends out from the outside surface of the front bracket (21). In the preferred embodiment, two C-clips (24, 25) are formed respectively near the upper and lower ends of the front bracket (21).

The clipping sheets (26) are mounted pivotally on the protrusions (211, 231) on the front and rear brackets (21, 23) between the two sides of the front and rear brackets (21, 23). Each clipping sheet (26) has two sides, an upper end, a lower end, an inside surface, an outside surface, a handhold (261) and a jaw (262). The handhold (261) is formed on the outside surface of the clipping sheet (26) near the upper end. The jaw (262) is formed on and protrudes out from the inside surface of the clipping sheet (26) adjacent to the lower end of the clipping sheet (26).

The inner cavity (27) is formed inside the connecting bracket (22), the front bracket (21), the clipping sheets (26) and the rear bracket (23) and has a bottom opening and an inside length. The bottom opening is formed opposite to the connecting bracket (22). The inside length is measured from the bottom opening to the connecting bracket (22) and may be adjusted by screwing the threaded adjustment plug (222) into or out of the threaded hole (221) in the connecting bracket (22).

Figure 4:
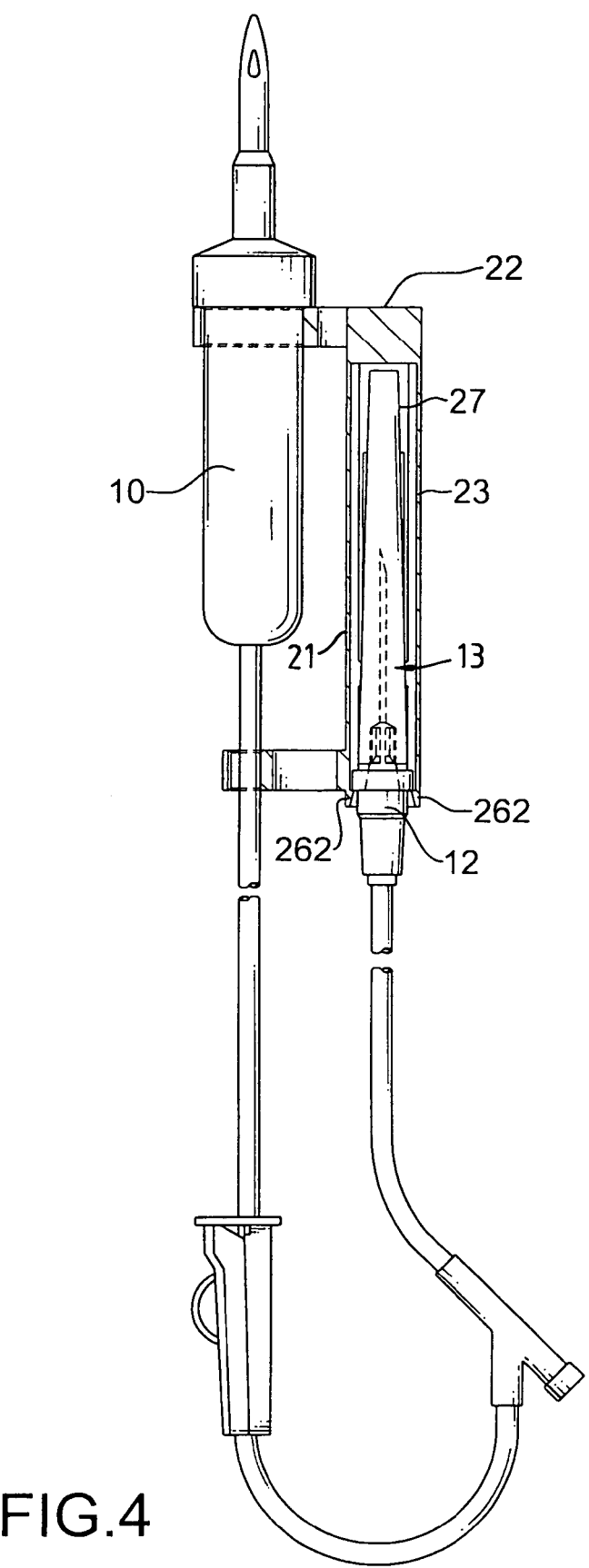
FIG. 4 is a side view in partial section of the intravenous drip assembly with the safety receptacle in FIG. 1.

With further reference to FIG. 4, a needle (12) in a tip protector (13) may be held in the inner cavity (27) of the safety receptacle (20). The tip protector (13) is clamped and is held between the jaws (262) on the clipping sheets (26). The flange (131) on the tip protector (13) is held between the limit (212) on the front bracket (21) and the jaws (262) on the clipping sheets (26). Therefore, the needle (12) can be removed from the tip protector (13) without taking the tip protector (13) out of the safety receptacle (20).

Figure 6:
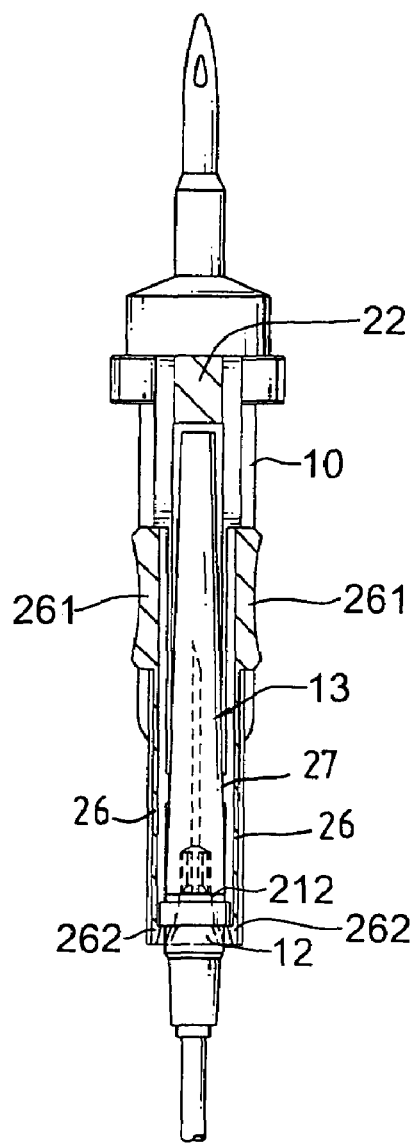
FIG. 6 is a rear view in partial section of the intravenous drip assembly with the safety receptacle in FIG. 1.
Figure 5:
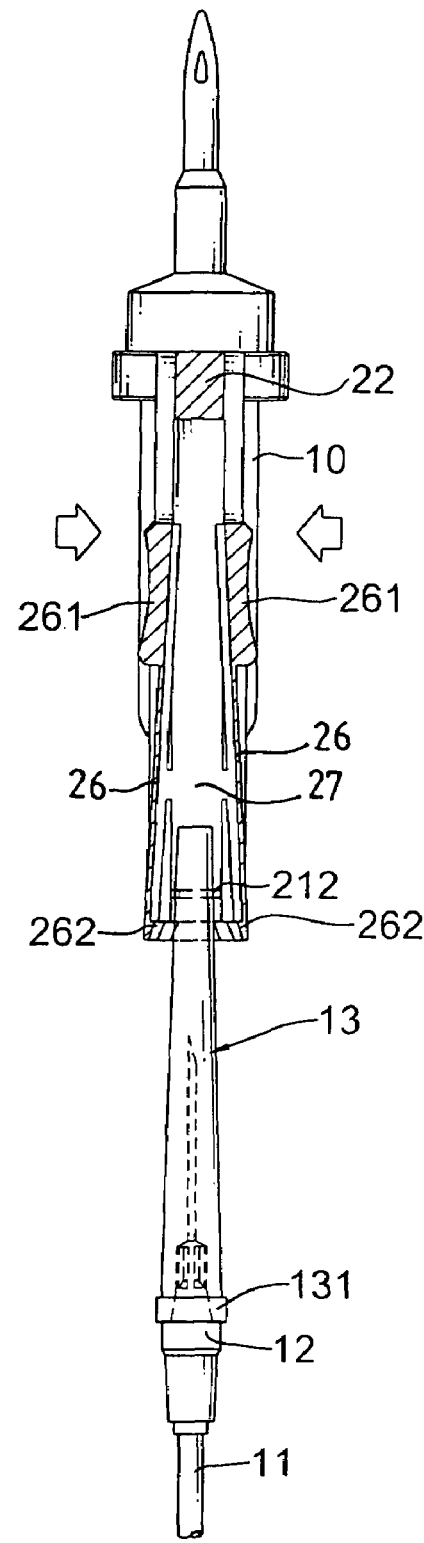
FIG. 5 is an operational rear view in partial section of the intravenous drip assembly with the safety receptacle in FIG. 1.

With further reference to FIGS. 5 and 6, the handholds (261) are pressed inward. The clipping sheets (26) are pivoted and the jaws (262) retract from the tip protector (13). Then the tip protector (13) can be removed from the inner cavity (27) of the safety receptacle (20).

With further reference to FIG. 7, the tip protector (13) is particularly long. The threaded adjustment plug (222) is screwed into the threaded hole (221) to adjust the length of the inner cavity (27) to fit the length of the tip protector (13).

The safety receptacle (20) as described has numerous advantages. The safety receptacle (20) can securely hold the needle (12) with the tip protector (13) to keep the needle (12) from accidentally stabbing a user. The needle (12) can be removed from the safety receptacle (20). Therefore, the needle (12) can be used again when the needle (12) is removed momentarily from a vein and needs to be inserted into the vein again.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A safety receptacle for a needle of an intravenous drip assembly comprising
   a front bracket having
      an upper end;
      a lower end;
      an outside surface;
      an inside surface;
      two sides;
      two protrusions formed on the inside surface near the lower end adjacent respectively to the two sides; and
      a limit formed on and extends out from the inside surface near the lower end;
   a connecting bracket formed on and extending transversely out from the inside surface of the front bracket adjacent to the upper end of the front bracket and having
      a front end formed on the inside surface of the front bracket; and
      a rear end;
   a rear bracket formed on and extending longitudinally out from the rear end of the connecting bracket and having
      an upper end;
      a lower end;
      an inside surface adjacent to the upper end of the rear bracket and formed on the rear end of the connecting bracket;
      two sides; and
      two protrusions formed on the inside surface of the rear bracket, adjacent respectively to the two sides of the rear bracket and corresponding to the protrusions on the front bracket;
   at least one C-clip formed on and extending out from the outside surface of the front bracket;
   two clipping sheets mounted pivotally on the protrusions on the front and rear brackets between the two sides of the front and rear brackets, and each clipping sheet having
      two sides;
      an upper end;
      a lower end;
      an inside surface;
      an outside surface;
      a handhold formed on the outside surface of the clipping sheet near the upper end; and
      a jaw formed on and protruding out from the inside surface of the clipping sheet adjacent to the lower end of the clipping sheet; and
   an inner cavity formed inside the connecting bracket, the front bracket, the clipping sheets and the rear bracket and having
      a bottom opening formed opposite to the connecting bracket; and
      an inside length measured from the bottom opening to the connecting bracket.

2. The safety receptacle as claimed in claim 1, wherein the connecting bracket has
   a threaded hole formed longitudinally through the connecting bracket; and
   a threaded adjustment plug screwed in the threaded hole
   the inside length of the inner cavity is adjusted by screwing the threaded adjustment plug into or out of the threaded hole.

3. The safety receptacle as claimed in claim 2, wherein the front bracket has two C-clips formed respectively near the upper and lower ends of the front bracket.

4. The safety receptacle as claimed in claim 1, wherein the front bracket has two C-clips formed respectively near the upper and lower ends of the front bracket.

* * * * *